(12) United States Patent
Marat et al.

(10) Patent No.: US 7,887,824 B2
(45) Date of Patent: Feb. 15, 2011

(54) SULFAMIDE DERIVATIVES AND COSMETIC USE THEREOF

(75) Inventors: Xavier Marat, Paris (FR); Benoit Muller, Paris (FR)

(73) Assignee: L'Oreal, Paris (FR)

( * ) Notice: Subject to any disclaimer, the term of this patent is extended or adjusted under 35 U.S.C. 154(b) by 1365 days.

(21) Appl. No.: 11/289,551

(22) Filed: Nov. 30, 2005

(65) Prior Publication Data

US 2006/0134151 A1 Jun. 22, 2006

Related U.S. Application Data

(60) Provisional application No. 60/638,371, filed on Dec. 27, 2004.

(30) Foreign Application Priority Data

Nov. 30, 2004 (FR) .................... 04 52821

(51) Int. Cl.
*C07C 311/49* (2006.01)
*C07C 311/48* (2006.01)
*A61K 8/46* (2006.01)
*A61K 8/44* (2006.01)
*C07C 311/50* (2006.01)

(52) U.S. Cl. ........................ 424/401; 568/28
(58) Field of Classification Search ................ 424/401; 568/28
See application file for complete search history.

(56) References Cited

U.S. PATENT DOCUMENTS 4,128,687 A 12/1978 Nachbur et al.
6,287,548 B1 9/2001 Biener

FOREIGN PATENT DOCUMENTS

| EP | 0 273 202 A2 | 7/1988 |
|---|---|---|
| EP | 0 549 079 A1 | 12/1992 |
| EP | 1 544 208 A1 | 8/2003 |
| FR | 2 355 896 | 1/1978 |
| IT | 463 449 | 5/1951 |
| JP | A-63-166837 | 7/1988 |
| JP | 07-097371 | 4/1995 |
| JP | A-07-267870 | 10/1995 |
| JP | 2004-196788 | 7/2004 |
| WO | WO 03/029226 A1 | 4/2003 |
| WO | WO 03/097589 A1 | 11/2003 |
| WO | WO 2004/050640 A1 | 6/2004 |

OTHER PUBLICATIONS

McManus et al. ,Journal of Medicinal Chemistry,1965, 8(6), pp. 766-776.*
Vippagunta et al. "Crystalline Solids," Advanced Drug Delivery Reviews, 2001, 48, 1-26, especially pp. 1, 11-12, and 18).*
Braga et a.,Chem. Commun., "Making Crystals from Crystals: a green route to crystal engineering and polymorphism," 2005, pp. 3635-3645.*
Seddon, K.R., "Pseudopolymorph: a polemic," Crystal Growth & Design, 2004, 4(6), pp. 1087, web release date Oct. 19, 2004.*
Loden M. et al., "A Double-Blind Study Comparing the Effect of Glycerin and Urea on Dry, Eczematous Skin in Atopic Patients", Acta Dermato-Venereologica, vol. 82, No. 1, 2002, pp. 45-47, XP001121921, ISSN: 0001-5555.
Yonekubo, Shigeru et al., "Human SGLT1 inhibitors containing benzylphenyl glucopyranoside or galactopyranoside derivatives," *Database CA* [Online] Chemical Abstracts Service, Abstract No. XP002336740 (2004) (Accession No. 2004:568609).
Alcaraz, Lilian et al., "Novel N-aryl and N-heteroaryl Sulfamide Synthesis via Palladium Cross-Coupling", Organic Letters, 2004, Vole 6. No. 16, pp. 2705-2708, Department of Medical Chemistry, Leics, United Kingdom.
Georges Dewynter et al., "Sulfonyl Bis-N-Oxazolidinone (SBO): A New Versatile Dielectrophile with Sequential Reactivity", Tetrahedron Letters, vol. 38, No. 50, pp. 8691-8694, 1997, Laboratoire de Chimie Biomoleculaire, Universite of Montpellier, Montpellier, France.
Joseph M. Dougherty et al., "Ring-Closing Metathesis Strategies to Cyclic Sulfamide Peptodomimetics", Tetrahedron 56, pp. 9781-9790, 2000, Department of Chemistry, University of Kansas, Kansas.
Matthew D. Reynolds et al., "A Concise Route to Structurally Diverse DMP 323 Analogues via Highly Funcitonalizcd 1, 4-Diamines", Organic Letters, vol. 4, No. 26, pp. 4673-4673, 2002, Department of Chemistry, University of Kansas, Lawrence, Kansas.

* cited by examiner

*Primary Examiner*—Johann R Richter
*Assistant Examiner*—Courtney Brown
(74) *Attorney, Agent, or Firm*—Oliff & Berridge, PLC

(57) ABSTRACT

The present invention relates to cosmetic compositions comprising a compound of formula (I)

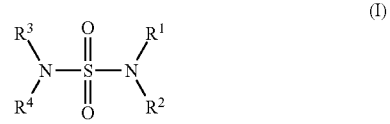

(I)

cosmetically acceptable salts thereof, solvates thereof and isomers thereof, that may be used in non-therapeutic skincare.

16 Claims, No Drawings

SULFAMIDE DERIVATIVES AND COSMETIC USE THEREOF

CROSS-REFERENCE TO RELATED APPLICATIONS

This non-provisional application claims the benefit of French Application No. 04 52821 filed on Nov. 30, 2004 and U.S. Provisional Application No. 60/638,371 filed on Dec. 27, 2004, the entire disclosures of which are incorporated herein by reference.

BACKGROUND

The present invention relates to a method for manufacturing a cosmetic composition comprising the use of sulfamides and derivatives thereof in the field of skincare and for example as a skin moisturizer, to novel sulfamide derivatives and to cosmetic compositions containing them.

The stratum corneum, which forms the interface with the dehydrating external environment, serves for example to delay the excessive loss of water originating from the deeper layers of the epidermis. The stratum corneum also protects against mechanical attack and the passage of chemical products and foreign microorganisms. It also constitutes the first line of defence against UV radiation.

The stratum corneum, which is 10 μm thick, is composed of vertically stacked corneocytes surrounded with a matrix of lipid-enriched membranes. Thus, it is a two-compartment system that may be compared with a brick wall, composed of anuclear cells (the "bricks") and of intercellular lamellar membranes (the "cement").

Urea is one of the ingredients widely used in moisturizing formulations. However, it can greatly modify the skin barrier by increasing the transepidermal water loss (TWL), which significantly reduces the barrier function of the stratum corneum.

Glycerol, another reference active agent in this field, has the drawback of making formulations tacky when it is used at high concentration.

There is thus a need to find alternative solutions in the field of skin moisturization.

SUMMARY

The inventors have discovered that certain sulfamide derivatives of general formula (I) described below may be good moisturizers and may have a beneficial effect in terms of elasticity on the stratum corneum.

Thus, in one exemplary embodiment, the present invention relates to a method for manufacturing a cosmetic composition comprising the use of compounds of general formula (I):

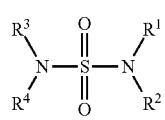

(I)

in which
$R^1$, $R^2$, $R^3$ and $R^4$ represent, independently of each other:
a hydrogen atom,
a $(C_1-C_{10})$alkyl group, for example a $(C_1-C_6)$alkyl group and for example a $(C_1-C_4)$alkyl group, optionally substituted with 1 to 5 groups chosen from —$OR^5$, —$NR^6R^7$ and —$SiR^8R^9R^{10}$, in which optionally 1 to 3 carbon atoms of the said $(C_1-C_{10})$alkyl group may be replaced, independently of each other, with a hetero atom chosen from a nitrogen atom, a sulfur atom, an oxygen atom, a silicon atom and a sulfonyl group (—$SO_2$—) including, for example, the group —O—$SO_2$—$NR^6R^7$, or alternatively ($R^1$ and $R^2$) and/or ($R^3$ and $R^4$) may form, with the nitrogen that bears them, a 5- to 7-membered heterocycle optionally substituted with 1 to 4 hydroxyl groups and/or a group —$NR^6R^7$, the heterocycle being chosen for example from pyrrolidine, piperazine, morpholine, azepane, pyrazolidine, imidazolidine and oxazolidine, and also partially unsaturated homologues thereof, for example pyrrole, pyridine or pyrimidine derivatives, or alternatively ($R^1$ and $R^3$) or ($R^2$ and $R^4$) may form, with the group —N—($SO_2$)—N— that bears them, a 5- to 9-membered heterocycle optionally substituted with 1 to 4 hydroxyl groups and/or a group $NR^6R^7$ and chosen for example from 1,2,5-thiadiazolidine, 1,2,6-thiadiazinane, 1,2,7-thiadiazepane, 1,2,8-thiadiazocane and 1,2,9-thiadiazonane 1,1-dioxides, $R^5$, $R^6$ and $R^7$ represent, independently of each other,
a hydrogen atom, or
a $(C_1-C_6)$alkyl group, and
$R^5$ may also represent a group such that —$OR^5$ represents a phosphate or sulfate group,
$R^8$, $R^9$ and $R^{10}$ represent, independently of each other, a $(C_1-C_6)$alkyl group,
and also the cosmetically acceptable salts thereof, solvates thereof such as hydrates, and isomers thereof, for non-therapeutic skincare, and for example as moisturizers, for example at a non-alkaline pH.

In another exemplary embodiment, the present invention relates to a cosmetic composition comprising a compound of formula (I), in a physiologically acceptable medium, for example at a non-alkaline pH.

In another exemplary embodiment, the present invention relates to a cosmetic composition comprising a compound of formula (I) as described above, with the exclusion of N,N'-bis(2-hydroxyethyl)sulfamide, in a physiologically acceptable medium, for example at a non-alkaline pH.

In another exemplary embodiment, the present invention relates to a cosmetic composition comprising, in a physiologically acceptable medium, for example at a non-alkaline pH, a compound of formula (I) as described above also comprising at least one additive chosen from an oil, a fatty substance, a gelling agent, a filler, a UV-screening agent, an odor absorber and a dyestuff.

In another exemplary embodiment, the present invention relates to a cosmetic treatment process for non-therapeutic skincare and/or for making up the skin, characterized in that it comprises the application to the skin of at least one cosmetic composition according to the present invention comprising a compound of formula (I) as defined above.

DETAILED DESCRIPTION OF EMBODIMENTS

Compounds of General Formula (I)

In the context of the present invention, an exemplary embodiment is the method for manufacturing a cosmetic composition comprising the use of the compounds of general formula (I) in which $R^1$, $R^2$, $R^3$ and $R^4$ represent, independently of each other:
a hydrogen atom,
a (2,2-dimethyldioxolane)methyl group,
a $(C_1-C_{10})$alkyl group optionally substituted with 1 to 5 groups chosen from $—OR^5$, $—NR^6R^7$ and $—SiR^8R^9R^{10}$, or alternatively ($R^1$ and $R^3$) or ($R^2$ and $R^4$) form, together with the $—N—(SO_2)—N—$ group that bears them, a 6- to 8-membered heterocycle chosen from 1,2,6-thiadiazinane, 1,2,7-thiadiazepane and 1,2,8-thiadiazonane 1,1-dioxides, optionally substituted with 1 to 3 hydroxyl groups, $R^5$ represents
a hydrogen atom,
a $(C_1-C_4)$alkyl group,
a group $—SO_2NRR'$, or
a group $—SiR^8R^9R^{10}$, $R^6$ and $R^7$ represent, independently of each other:
a hydrogen atom, or
a $(C_1-C_4)$alkyl group, $R^8$, $R^9$ and $R^{10}$ represent, independently of each other, a $(C_1-C_4)$alkyl group, and R and R' represent, independently of each other, a hydrogen atom or a $(C_1-C_4)$ alkyl group, and also the cosmetically acceptable salts thereof, solvates thereof such as hydrates and isomers thereof, for non-therapeutic skincare, and for example as moisturizers, for example at a non-alkaline pH.

These compounds of formula (I) will be referred to hereinbelow as "compounds A", for reasons of simplicity.

Another exemplary embodiment is the method for manufacturing a cosmetic composition comprising the use of the compounds of general formula (I) in which $R^1$, $R^2$, $R^3$ and $R^4$ represent, independently of each other:
a hydrogen atom,
a $(C_1-C_6)$alkyl group optionally substituted with 1 to 5 hydroxyl groups, 1 or 2 $—SiMe_3$ groups or with a group $—O—SO_2NRR'$, or alternatively ($R^1$ and $R^3$) represent a hydrogen atom and ($R^2$ and $R^4$) together form, with the $—N—(SO_2)—N—$ group that bears them, a 1,2,7-thiadiazepane 1,1-dioxide group optionally substituted with 1 or 2 hydroxyl groups or a 1,2,6-thiadiazinane 1,1-dioxide group optionally substituted with 1 or 2 hydroxyl groups, R and R' represent, independently of each other:
a hydrogen atom, or
a $(C_1-C_4)$alkyl group, and also the cosmetically acceptable salts thereof, solvates thereof such as hydrates, and isomers thereof, for non-therapeutic skincare, and for example as moisturizers, for example at a non-alkaline pH.

These compounds of formula (I) will be referred to hereinbelow as "compounds B", for reasons of simplicity.

In the context of the present invention, the term "alkyl" means a linear or branched, saturated or unsaturated, cyclic or non-cyclic hydrocarbon-based chain. Among the alkyl groups that are suitable for use in the invention, mention may be made for example of the methyl, ethyl, isopropyl, n-propyl, n-butyl, t-butyl, $—CH_2$-t-butyl, pentyl, n-hexyl, cyclopropyl, cyclopentyl, cyclohexyl, cyclohexylmethyl, heptyl, octyl, nonyl, decyl, norbornyl and adamantyl groups.

Among the $(C_1-C_{10})$alkyl groups in which 1 to 3 carbon atoms may be replaced with a hetero atom, mention may be made of the (2,2-dimethyldioxolane)methyl group.

In the context of the present invention, the term "non-alkaline pH" means a pH of between 4 and 7 and for example between 5 and 6.

Some of the compounds of formula (I) are known. The following documents describe some of them and give useful indications regarding the modes of synthesis described below.

L. F. Audrieth; M. Sveda, H. Sisler, M. Josetta Butler, Chemical Review, 1940, 26, 49-94, Paquin, Angewante Chemie, 1948, 60, 11/12, 316-320, K. Sprott, P. Hanson, Journal of Organic Chemistry, 2000, 65, 7913-7918, M. McReynolds, K. Sprott, P. Hanson, Organic Letters, 2002, 4, 26, 4673-4676, H. Preuschhof, H-U. Heyne, Organic Syntheses, Collective volume 6, 78, step 1, J. M. Dougherty, D. A. Probst, R. E. Robinson, J. D. Moore, T. A. Klein, K. A. Snelgrove, P. R. Hanson, Tetrahedron, 2000, 56, 9781-9790, G. Dewynter, M. Abdaoui, L. Toupet, J-L. Montero, Tetrahedron Letters, 1997, 38, 8691-8694, and Y. Masui, H. Watanabe, T. Masui, Tetrahedron Letters, 2004, 45, 1853-1856, G. M. Atkins, E. M. Burgess, Journal of the American Chemical Society, 1968, 90, 4744-4745.

Compounds According to the Invention and Preparation Thereof

The compounds of formulae (II), (III) and (IV) defined below also form part of the invention.

According to one exemplary embodiment, the invention is related to compounds of formula (II)

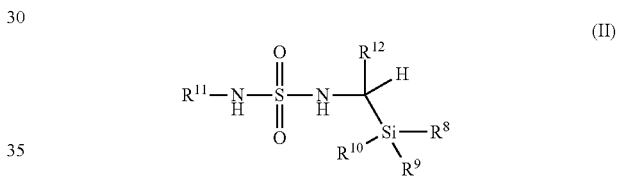

in which:

$R^{12}$ represents a hydrogen atom, a group $—SiR^8R^9R^{10}$, a $(C_1-C_9)$alkyl group optionally substituted with 1 to 5 groups chosen from $—OR^5$, $—NR^6R^7$ and $—SiR^8R^9R^{10}$, in which optionally 1 to 3 carbon atoms of the said $(C_1-C_9)$alkyl group may be replaced, independently of each other, with a hetero atom chosen from a nitrogen atom, a sulfur atom, an oxygen atom and a silicon atom or a sulfonyl group $(—SO_2—)$, $R^{11}$ represents a hydrogen atom, a $(C_1-C_6)$alkyl group optionally substituted with 1 to 5 groups chosen from $—OR^5$ and/or $—SiR^8R^9R^{10}$ or optionally with a group $—OSO_2—NRR'$, $R^5$, $R^6$, $R^7$, $R^8$, $R^9$, $R^{10}$, R and R' being as defined above for the compounds A and the compounds B of formula (I), and also the solvates thereof such as hydrates, salts thereof and isomers thereof.

In one exemplary embodiment, the compounds of formula (II) are those in which:

$R^{12}$ represents a hydrogen atom, an $—SiMe_3$ group or a $(C_1-C_6)$alkyl group optionally substituted with 1 to 5 hydroxyl groups, 1 or 2 $—SiMe_3$ groups or with an $—O—SO_2NH_2$ group, $R^{11}$ represents a hydrogen atom or a $(C_1-C_6)$alkyl group optionally substituted with 1 or 2 groups chosen from $—OR^5$ and $—SiMe_3$, $R^5$, $R^8$, $R^9$ and $R^{10}$ being as defined above for the compounds A and the compounds B of formula (I), and also the solvates thereof such as the hydrates, salts thereof and isomers thereof.

In one exemplary embodiment, the compounds of formula (II) are those in which:

$R^{12}$ represents a hydrogen atom, an —SiMe$_3$ group or a (C$_1$-C$_6$)alkyl group optionally substituted with a hydroxyl group, $R^{11}$ represents a hydrogen atom or a (C$_1$-C$_6$)alkyl group optionally substituted with 1 or 2 hydroxyl groups, and $R^8$, $R^9$ and $R^{10}$ each represent a methyl group, and also solvates thereof such as hydrates, salts thereof and isomers thereof.

According to another exemplary embodiment, the invention relates to the compounds of formula (III)

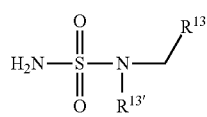

(III)

in which:

$R^{13}$ represents a (C$_1$-C$_9$)alkyl substituted with 1 to 5 groups chosen from —OR$^5$ and —NR$^6$R$^7$, or a group —O—SO$_2$NRR', $R^{13'}$ represents a hydrogen atom or a (C$_1$-C$_4$)alkyl group, and $R^5$, $R^6$ and $R^7$ are as defined above for the compounds A and the compounds B of formula (I), R and R' being as defined above for the compounds A and the compounds B of formula (I), and also solvates thereof such as hydrates, salts thereof and isomers thereof.

In one exemplary embodiment, the invention relates to the compounds of formula (III) in which $R^{13}$ represents a (C$_1$-C$_9$)alkyl substituted with 1 to 5 groups chosen from —OR$^5$ and a group —O—SO$_2$NRR', $R^5$ representing a hydrogen atom, a (C$_2$-C$_4$)alkyl group, a group —SO$_2$NRR', or a group —SiR$^8$R$^9$R$^{10}$ with $R^8$, $R^9$, $R^{10}$, R and R' being as defined above for the compounds A and the compounds B of formula (I).

In one exemplary embodiment, the compounds of formula (III) are those in which:

$R^{13}$ represents a (C$_1$-C$_9$)alkyl group substituted with 1 to 5 hydroxyl group(s) or with an —O—SO$_2$NH$_2$ group, and $R^{13'}$ represents a hydrogen atom or a methyl group, and also solvates thereof such as hydrates, salts thereof and isomers thereof.

According to yet another exemplary embodiment, the invention relates to the compounds of formula (IV)

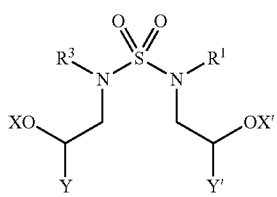

(IV)

in which:

X and X' take, independently of each other, the meaning of $R^5$ as defined above for the compounds of formula (I) and Y and Y' represent, independently of each other, a hydrogen atom, a group —CH$_2$Z, in which Z represents an amine group or a group —NR$^6$R$^7$ or —OR$^5$, or alternatively at least one of the groups

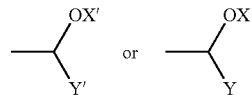

forms, independently of each other, a dimethyldioxolane group, or alternatively:

X and X' are hydrogen atoms and Y and Y' together form a covalent bond, $R^1$, $R^3$, $R^5$, $R^6$ and $R^7$ take the same meaning as that defined for the compounds of formula (I), and X, X', Y and Y' advantageously do not simultaneously represent a hydrogen atom.

A subject of the invention is, for example, the compounds of formula (IV) in which Y and Y' are not simultaneously a hydrogen atom when X and X' simultaneously represent a —CH$_3$ group.

According to one exemplary embodiment, the compounds of formula (IV) are those in which:

X and X' are hydrogen atoms and Y and Y' represent a group

—CH$_2$OR$^5$, or alternatively at least one of the groups

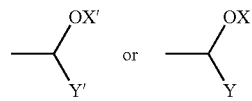

forms a dimethyldioxolane group, or alternatively

X and X' are hydrogen atoms and Y and Y' together form a covalent bond, and $R^1$, $R^3$ and $R^5$ take the same meaning as that defined by the compounds of formula (I).

In one exemplary embodiment, the compounds of formula (IV) are those in which:

X and X' are hydrogen atoms and Y and Y' represent a —CH$_2$OH group, or alternatively X and X' are hydrogen atoms and Y and Y' together form a covalent bond, and $R^1$ and $R^3$ represent a hydrogen atom or a (C$_1$-C$_6$)alkyl group.

The salts that are acceptable for the non-therapeutic use of the compounds described in the present invention include the conventional non-toxic salts of the said compounds, such as those formed from organic or mineral acids. Examples that may be mentioned include the salts of mineral acids, such as sulfuric acid, hydrochloric acid, hydrobromic acid, hydriodic acid, phosphoric acid or boric acid. Mention may also be made of the salts of organic acids, which may comprise one or more carboxylic, sulfonic or phosphonic acid groups. They may be linear, branched or cyclic aliphatic acids or alternatively aromatic acids. These acids may also comprise one or more hetero atoms chosen from O and N, for example in the form of hydroxyl groups. Mention may be made for example of propionic acid, acetic acid, terephthalic acid, citric acid and tartaric acid.

When the compound of formula (I) comprises an acid group, the neutralization of the acid group(s) may be performed with a mineral base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made especially of 2-amino-2-methylpropanol, triethanolamine, 2-dimethylaminopropanol and 2-amino-2-(hydroxymethyl)-1,3-propanediol. Mention may also be made of lysine or 3-(dimethylamino)propylamine.

The solvates that are acceptable for the non-therapeutic use of the compounds described in the present invention include conventional solvates such as those formed during the final step of preparation of the said compounds, due to the presence of solvents. Examples that may be mentioned include the solvates due to the presence of water or of linear or branched alcohols, for instance ethanol or isopropanol.

The compounds of formula (I) may be prepared according to techniques that are well known to those skilled in the art, for example according to a scheme 1 described below.

The standard modes for obtaining sulfamide are performed starting with sulfuryl chloride.

The amines (or diamines) chosen to give the compounds of formula (I) may be reacted (sequentially for the dissymmetric compounds) with an electrophilic source of $SO_2$, such as sulfamide $H_2NSO_2NH_2$, sulfuryl chloride $SO_2Cl_2$, or sulfonylbis(2-oxazolidine) in a suitable solvent (for example, respectively, acetonitrile, pyridine or dimethylformamide for sulfamide, or, for example, dichloromethane or tetrahydrofuran for sulfuryl chloride), for example at a temperature ranging from 0 to 140° C. in the presence or absence of a base, for instance diazabicycloundecene, triethylamine or pyridine.

Scheme 1

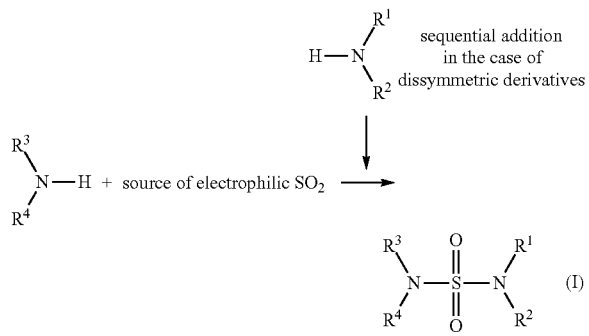

Methods for synthesizing the novel compounds of formulae (II), (III) and (IV), respectively, are detailed below.

Compounds of formula (II) may be prepared according to scheme 2 below:

Scheme 2

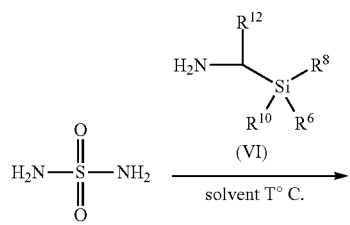

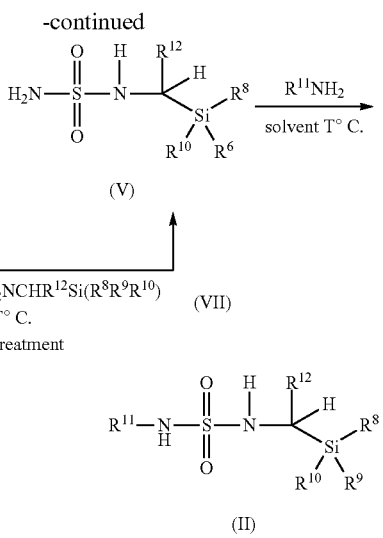

The compounds (II) may be obtained in two ways:

either using sulfamide by reacting one mole of silyl amine of formula (VI), for example in a polar solvent such as acetonitrile, dimethylformamide or pyridine, for example at a temperature of between 0 and 140° C. in the presence or absence of a catalytic amount of base, for instance diazabicycloundecene, to give the compounds of formula (V), followed by a second addition of one mole of amine $R^{11}NH_2$, for example under similar conditions, or using chlorosulfonyl isocyanate by performing a sequential addition of tert-butanol and of silyl amine of formula (VII), for example, in a solvent such as dichloromethane or ethyl acetate, for example between 0 and 20° C. in the presence of a base, for instance triethylamine or pyridine, in order to obtain a dissymmetric sulfamide in which the $NH_2$ group, protected in the form of tert-butoxycarbonyl, is released by means of an acidic treatment with, for example, hydrochloric acid or trifluoroacetic acid; compound (II) may then be formed via addition of one mole of amine of formula $R^{11}NH_2$ in a polar solvent such as acetonitrile, dimethylformamide or pyridine, for example at a temperature of between 0 and 140° C. and in the presence or absence of a catalytic amount of base, for instance diazabicycloundecene.

The compounds of formula (III) may be prepared according to scheme 3 below:

Scheme 3

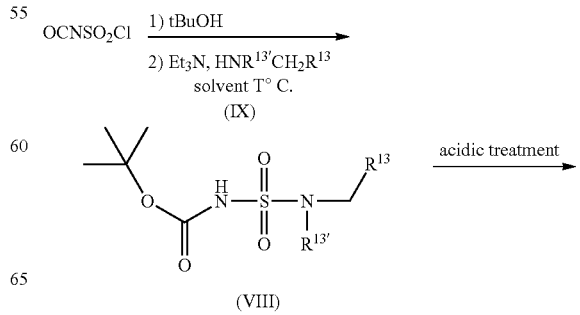

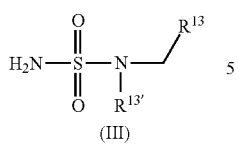

Chlorosulfonyl isocyanate is sequentially reacted with one mole of tert-butanol, followed by one mole of amine of formula (IX) in the presence of a base such as triethylamine or pyridine, for example in a solvent such as dichloromethane or ethyl acetate, for example at a temperature of between 0 and 20° C. The N-protected compound of formula (VIII) in tert-butoxycarbonyl form is then deprotected in acidic medium with, for example, hydrochloric acid or trifluoroacetic acid, for example at room temperature, to give the compounds of formula (III).

The compounds of formula (IV) may be prepared according to scheme 4, which is a particular form of scheme 1:

Scheme 4

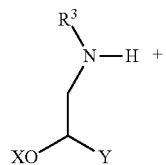

The amines (or diamines) of respective formulae (X) and (XI) chosen to give the compounds of formula (IV) are reacted (sequentially for the dissymmetric compounds) with an electrophilic source of $SO_2$, such as sulfamide $H_2NSO_2NH_2$, sulfuryl chloride $SO_2Cl_2$, or sulfonylbis(2-oxazolidine), in a suitable solvent (for example, respectively, acetonitrile, pyridine or dimethylformamide for sulfamide, or, for example, dichloromethane or tetrahydrofuran for sulfuryl chloride), for example at a temperature ranging from 0 to 140° C. in the presence or absence of a base, for instance diazabicycloundecene, triethylamine or pyridine.

The table below collates the compounds that may preferably be used in the context of the present invention.

TABLE 1

| No. | Chemical name | Formula |
|---|---|---|
| 1 | Sulfamide | $H_2N-S(=O)_2-NH_2$ |
| 2 | N-(2-hydroxyethyl)sulfamide | $H_2N-S(=O)_2-NH-CH_2CH_2-OH$ |
| 3 | N-(3-hydroxypropyl)sulfamide | $H_2N-S(=O)_2-NH-CH_2CH_2CH_2-OH$ |

TABLE 1-continued

| No. | Chemical name | Formula |
|---|---|---|
| 4 | N-(2,3-dihydroxypropyl)sulfamide | 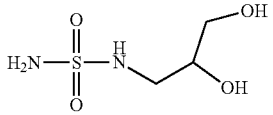 |
| 5 | N-(4-hydroxybutyl)sulfamide | 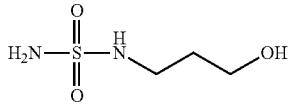 |
| 6 | N-(2,3,4,5,6-penta-hydroxyhexyl)sulfamide | 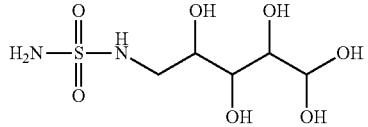 |
| 7 | N-Methyl-N-(2,3,4,5,6-penta-hydroxyhexyl)sulfamide | 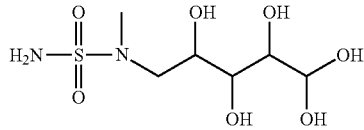 |
| 8 | N-[trimethylsilylmethyl]sulfamide | 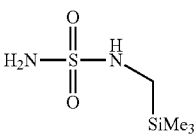 |
| 9 | N-[bis(trimethylsilyl)methyl]sulfamide | 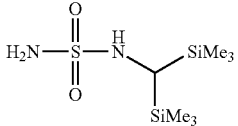 |
| 10 | N, N''-bis(hydroxyethyl)sulfamide | 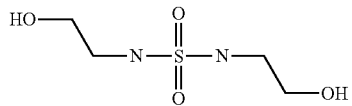 |
| 11 | N, N''-bis(hydroxypropyl)sulfamide | 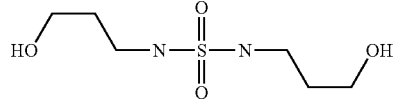 |
| 12 | N, N''-bis(hydroxybutyl)sulfamide | 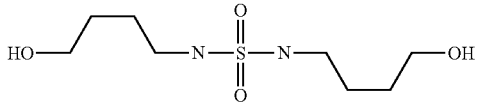 |
| 13 | N, N''-bis(2,3-dihydroxypropyl)sulfamide | 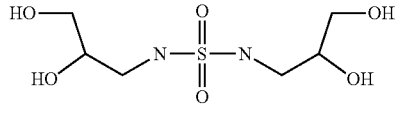 |
| 14 | N,N''-bis[(2,2-dimethyl-1,3-dioxolan-4-yl)methyl]sulfamide | 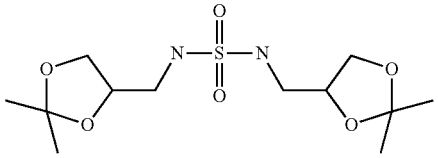 |

TABLE 1-continued

| No. | Chemical name | Formula |
|-----|---------------|---------|
| 15 | N-[bis(trimethylsily)methyl]-N''-(2-hydroxyethyl)sulfamide | *(structure)* |
| 16 | N-[(trimethylsilyl)methyl]-N''-(2-hydroxyethyl)sulfamide | *(structure)* |
| 17 | 2-[(aminosulfonyl)amino]ethyl sulfamate | *(structure)* |
| 18 | 3-[(aminosulfonyl)amino]propyl sulfamate | *(structure)* |
| 19 | (+/−) 1,2,7-thiadiazepane-4,5-diol 1,1-dioxide | *(structure)* |

Cosmetic Formulations

In one exemplary embodiment, the present invention relates to a cosmetic composition comprising a compound of formula (I) as described above, with the exclusion of N,N'-bis(2-hydroxyethyl)sulfamide, in a physiologically acceptable medium, for example at a non-alkaline pH.

In one exemplary embodiment, the present invention relate to a cosmetic composition comprising, in a physiologically acceptable medium, for example at a non-alkaline pH, a compound of formula (I) as described above also comprising at least one additive chosen from an oil, a fatty substance, a gelling agent, a filler, a UV-screening agent, an odor absorber and a dyestuff.

These cosmetic compositions in which the compounds (I), (II), (III) or (IV) may be used are useful for non-therapeutic skincare and/or for making up the skin. They are useful for example for moisturizing the skin.

They may show their efficacy as a non-therapeutic, i.e. a preventive, skin maintenance treatment. They may also be used as a non-therapeutic skin treatment after the appearance of skin moisturization disorders.

In this second case, this appearance of skin moisturization disorders may be for example independent of irritation caused by the placing in contact of the skin with a bleaching agent, for example a chlorinated bleaching agent, for example based on hypochlorite.

In addition, the said cosmetic compositions may be for example not used for hygiene, purposes, and for example they preferably do not contain any detergent.

Finally, the cosmetic compositions of the invention may be for example formulated under non-alkaline conditions, for example at a pH close to that of the skin, for example at a pH of between 5 and 6.

The compounds of formula (I), (II), (III) or (IV) may be present in the cosmetic compositions in contents ranging from 0.01% to 20%, for example from 0.01% to 15% and for example from 0.1% to 10% by weight relative to the total weight of the cosmetic composition.

The compositions used according to the invention contain a physiologically acceptable medium, i.e. a medium that is compatible with skin tissues such as the skin and the scalp. This physiologically acceptable medium may consist for example of water and optionally of a physiologically acceptable organic solvent chosen, for example, from lower alcohols containing from 1 to 8 carbon atoms and for example from 1 to 6 carbon atoms, for instance ethanol, isopropanol, propanol or butanol; polyethylene glycols containing from 6 to 80 ethylene oxide units and polyols, for instance propylene glycol, isoprene glycol, butylene glycol, glycerol and sorbitol.

The compositions according to the invention may be in any galenical form conventionally used for topical application, and for example in the form of aqueous or aqueous-alcoholic solutions, oil-in-water (O/W) emulsions, water-in-oil (W/O) emulsions or multiple emulsions (triple: W/O/W or O/W/O), aqueous gels, or dispersions of a fatty phase in an aqueous phase by means of spherules, these spherules possibly being polymer nanoparticles such as nanospheres and nanocapsules or lipid vesicles of ionic and/or nonionic type (liposomes, niosomes or oleosomes). These compositions are prepared according to the usual methods.

In addition, the compositions used according to the invention may be more or less fluid and may have the appearance of a white or coloured cream, a pomade, a milk, a lotion, a serum, a paste or a mousse. They may be optionally applied to the skin in aerosol form. They may also be in solid form, for example in the form of a stick.

When the composition used according to the invention comprises an oily phase, it contains for example at least one oil. It may also contain other fatty substances.

As examples of oils that may be used in the composition of the invention, mention may be made of:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names "Miglyol 810", "812" and "818" by the company Dynamit Nobel, jojoba oil or shea butter oil;

synthetic esters and synthetic ethers, for example of fatty acids, for instance oils of formulae $R_1COOR_2$ and $R_1OR_2$ in which $R_1$ represents the fatty acid residue containing from 8 to 29 carbon atoms and $R_2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile paraffin oils, and derivatives thereof, petroleum jelly, polydecenes, and hydrogenated polyisobutene such as Parleam oil;

fatty alcohols containing from 8 to 26 carbon atoms, for instance cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or partially silicone-based fluoro oils, for instance those described in document JP-A-2 295 912;

silicone oils, for instance volatile or non-volatile polymethylsiloxanes (PDMSs) containing a linear or cyclic silicone chain, that are liquid or pasty at room temperature, for example cyclopolydimethylsiloxanes (cyclomethicones) such as cyclohexasiloxane; polydimethylsiloxanes comprising alkyl, alkoxy or phenyl groups, that are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin, beeswax, carnauba wax or candelilla wax, paraffin wax, lignite wax or microcrystalline waxes, ceresin or ozokerite, synthetic waxes such as polyethylene waxes, Fischer-Tropsch waxes; silicone resins such as trifluoromethyl-C1-4-alkyl dimethicone and trifluoropropyl dimethicone; and silicone elastomers, for instance the products sold under the name "KSG" by the company Shin-Etsu, under the name "Trefil", "BY29" or "EPSX" by the company Dow Corning, or under the name "Gransil" by the company Grant Industries.

These fatty substances may be chosen in a varied manner by a person skilled in the art so as to prepare a composition having the desired properties, for example in terms of consistency or texture.

According to one exemplary embodiment of the invention, the composition according to the invention is a water-in-oil (W/O) or oil-in-water (O/W) emulsion. The proportion of the oily phase of the emulsion may range from 5% to 80% by weight and for example from 5% to 50% by weight relative to the total weight of the composition.

The emulsions may contain at least one emulsifier chosen from amphoteric, anionic, cationic and nonionic emulsifiers, used alone or as a mixture, and optionally a co-emulsifier. The emulsifiers are chosen in a suitable manner depending on the emulsion to be obtained (W/O or O/W). The emulsifier and the co-emulsifier may be present in the composition in a proportion that may range, for example, from 0.3% to 30% by weight and for example from 0.5% to 20% by weight relative to the total weight of the composition.

Examples of emulsifiers that may be mentioned for the W/O emulsions include dimethicone copolyols such as the mixture of cyclomethicone and of dimethicone copolyol, sold under the name "DC 5225 C" by the company Dow Corning, and alkyldimethicone copolyols, such as the laurylmethicone copolyol sold under the name "Dow Corning 5200 Formulation Aid" by the company Dow Corning, and the cetyldimethicone copolyol sold under the name "Abil EM 90®" by the company Goldschmidt. Surfactants for W/0 emulsions that may also be used include a crosslinked elastomeric solid organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, for example the product of Example 3 (synthesis example) of U.S. Pat. No. 5,412,004, and such as the product sold under the reference KSG 21 by the company Shin-Etsu.

Examples of emulsifiers that may be mentioned for the O/W emulsions include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters, for instance sucrose stearate; and mixtures thereof, such as the mixture of glyceryl stearate and of PEG-40 stearate.

In a known manner, the cosmetic or dermatological composition of the invention may also contain adjuvants that are common in cosmetics or dermatology, such as gelling agents, film-forming polymers, preserving agents, solvents, fragrances, fillers, UV-screening agents, bactericides, odor absorbers, dyestuffs, plant extracts and salts. The amounts of these various adjuvants are those conventionally used in the field under consideration, for example from 0.01% to 20% of the total weight of the composition. Depending on their nature, these adjuvants may be introduced into the fatty phase and/or into the aqueous phase.

The compounds of formulae (I), (II), (III) and (IV) may be combined together, or with other skin moisturizers not in accordance with formula (I) and/or with at least one other cosmetic active agent.

Additional cosmetic active agents that may for example be mentioned include active agents acting on the barrier function of the skin, active agents that promote skin moisturization and desquamating agents.

The term "desquamating agent" means any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of Saphora japonica; resveratrol;

or on the enzymes involved in the desquamation or degradation of corneodesmosomes, such as glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; aminosulfonic compounds and for example (N-2-hydroxyethylpiperazine-N'-2-ethane) sulfonic acid (HEPES); 2-oxothiazolidine-4-carboxylic acid (procysteine) derivatives; α-amino acid derivatives of the type such as glycine (as described in EP-0 852 949 and sodium methylglycinediacetate sold by BASF under the trade name "Trilon M"); honey; sugar derivatives such as O-octanoyl-6-D-maltose and N-acetylglucosamine.

Among the active agents acting on the barrier function of the skin, or that promote skin moisturization, mention may be made of:

either a compound acting on the barrier function, in order to keep the stratum corneum moisturized, or an occlusive compound, for example ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes such as ursolic acid, petroleum jelly and lanolin;

or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-α-benzoyl-L-arginine;

or a compound that activates the sebaceous glands, such as steroid derivatives (including DHEA) and vitamin D and its derivatives.

The composition may be in the form of a non-therapeutic care and/or makeup product, and also in the form of a lip balm.

In yet one exemplary embodiment, the invention relates to a cosmetic treatment process for non-therapeutic skincare and/or for making up the skin, characterized in that it comprises the application to the skin of at least one cosmetic composition according to the present invention comprising at least one compound of formula (I), (II), (III) or (IV) as defined above or a mixture thereof in all proportions.

Among the applications of makeup type that may be envisaged by means of the cosmetic treatment process, mention may be made for example of foundations, makeup rouges, eyeshadows, concealer products and body makeup products.

In another exemplary embodiment, the invention relates to a method for preparing a dermatological composition for moisturizing the skin and for example for treating dryness of the skin or for treating dry skin comprising the use of a compound of formula (I), (II), (III) or (IV) as defined above, or a mixture thereof.

The examples below illustrate the invention without, however, limiting its scope.

The elemental analyses and the NMR spectra confirm the structures of the products obtained.

The numbers given in parentheses in the example titles correspond to those in Table 1 given above.

Example 1

Synthesis of N,N"-(2,3-dihydroxypropyl)sulfamide (Compound 13)

To a solution of 1.55 ml of methamine dioxolane in 25 ml of dichloromethane and 1.84 ml of triethylamine are added dropwise, at 0° C., 482 µl of sulfuryl chloride. After addition, the reaction mixture is warmed slowly to 20° C. The reaction mixture is diluted with dichloromethane and washed with water and then with saturated sodium chloride solution. The organic phase is dried over sodium sulfate and then concentrated under reduced pressure to give 1.6 g of a white solid identified as N,N"-bis[(2,2-dimethyl-1,3-dioxolan-4-yl)methyl]sulfamide.

This compound, N,N"-bis[(2,2-dimethyl-1,3-dioxolan-4-yl)methyl]sulfamide, is then suspended in water in the presence of Dowex® 50WX8 acidic resin sold by Aldrich. The reaction medium dissolves rapidly and the reaction progress is monitored by thin-layer chromatography. Once the reaction is complete, the mixture is filtered and the filtrate is evaporated under vacuum to give a vitrified oil, which is taken up in a mixture of ether and methanol to give 1.16 g of a white solid recovered by filtration and identified as N,N"-(2,3-dihydroxypropyl)sulfamide.

Melting point: 80-81° C. (ether/methanol).

| % | Elemental analysis: | | | | |
|---|---|---|---|---|---|
| | C | H | N | O | S |
| Calculated | 29.5 | 6.6 | 11.5 | 39.5 | 13.1 |
| Experimental | 29.6 | 6.6 | 11.3 | 39.2 | 13.1 |

Example 2

Synthesis of 2-[(aminosulfonyl)amino]ethyl sulfamate (Compound 17)

To 4.35 ml of chlorosulfonyl isocyanate in 25 ml of dichloromethane is added dropwise, at 0° C., a solution of 4.78 ml of tert-butanol in 25 ml of dichloromethane. The reaction medium is stirred for 10 minutes at 20° C. and is then added dropwise to a solution of 3.01 ml of ethanolamine and 7.66 ml of triethylamine in 60 ml of dichloromethane at 0° C. After raising the temperature to 20° C. and stirring overnight, the reaction mixture is diluted with dichloromethane and washed 3 times with dilute hydrochloric acid. The organic phase is then washed 3 times with water and is then dried over sodium sulfate and concentrated under reduced pressure to give 5 g of a white solid identified as 2-({[(tert-butoxycarbonyl)amino]sulfonyl}amino)ethyl tert-butoxycarbonylsulfamate, which may be used in unmodified form.

To 1.5 g of 2-({[(tert-butoxycarbonyl)amino]sulfonyl}amino)ethyl tert-butoxycarbonylsulfamate in 30 ml of dichloromethane are added 30 ml of a 1/1 trifluoroacetic acid/dichloromethane mixture. After stirring for 4 hours at 20° C., the reaction mixture is concentrated under reduced pressure and taken up 3 times in ether and reevaporated. The white solid is taken up in dichloromethane and filtered under vacuum to give 700 mg of the desired product: 2-[(aminosulfonyl)amino]ethyl sulfamate.

Melting point: 78-82° C. (ether/dichloromethane).

| Elemental analysis: | | | | | |
|---|---|---|---|---|---|
| % | C | H | N | O | S |
| Calculated | 11 | 4.1 | 19.2 | 36.5 | 29.3 |
| Experimental | 11.7 | 4.2 | 18.6 | 35.1 | 29.4 |

Example 3

Synthesis of (±)-1,2,7-thiadiazepane-4,5-diol 1,1-dioxide (Compound 19)

To 1.5 g of (±)-4,5-di(aminomethyl)-2,2-dimethyl dioxolane in 30 ml of dimethylformamide are added 1.08 g of sulfamide and 301 µl of diazabicycloundecene. The reaction mixture is then heated at 140° C. for several hours until conversion is complete. After evaporating off the dimethylformamide, the crude reaction product is chromatographed on a column of silica to give 1.5 g of an orange solid. This solid is then taken up in pentane to give 1.2 g of a solid identified as 2,2-dimethylhexahydro[1,3]dioxolo[4,5-d][1,2,7]thiadiazepine 6,6-dioxide.

To 500 mg of 2,2-dimethylhexahydro[1,3]dioxolo[4,5-d][1,2,7]thiadiazepine 6,6-dioxide suspended in 10 ml of water are added Dowex® 50WX8 acidic resin, sold by Aldrich, and 2 ml of tetrahydrofuran. The reaction medium is stirred at room temperature overnight to give, after filtering off the resin and evaporating off the water, a vitrified paste that is taken up in ether and methanol to give 380 mg of a pale yellow solid identified as (±)-1,2,7-thiadiazepane-4,5-diol 1,1-dioxide.

Melting point: 188-192° C. (ether/methanol)

| Elemental analysis: | | | | | |
|---|---|---|---|---|---|
| % | C | H | N | O | S |
| Calculated | 26.4 | 5.5 | 15.4 | 35.1 | 17.6 |
| Experimental | 26.5 | 5.5 | 15.3 | 34.7 | 17.6 |

Example 4

Synthesis of N-(2-hydroxyethyl)sulfamide (Compound 2)

To 2.17 ml of chlorosulfonyl isocyanate in 10 ml of dichloromethane is added dropwise, at 0° C., a solution of 2.39 ml of tert-butanol in 10 ml of dichloromethane. The reaction medium is stirred for 30 minutes at 0° C., followed by dropwise addition of 10.4 ml of triethylamine. After stirring for 30 minutes, 1.58 ml of ethanolamine are added dropwise at 0° C.

After warming to 20° C. and stirring overnight, the reaction mixture is concentrated under vacuum and the crude product is then diluted with dichloromethane and water and also with 0.1N hydrochloric acid. The aqueous phase is then acidified with 1N hydrochloric acid and extracted three times with ethyl acetate. The organic phases are washed with saturated sodium chloride solution and then dried over sodium sulfate. After evaporation, 2.5 g of a white solid are obtained, dried under vacuum and identified as N (tert-butoxycarbonyl)-N"-(2-hydroxyethyl)sulfamide.

1 g of N-(tert-butoxycarbonyl)-N"-(2-hydroxyethyl)sulfamide is suspended in 10 ml of 1N hydrochloric acid with stirring at room temperature. After reacting overnight, the reaction monitored by thin-layer chromatography is complete. The reaction medium is concentrated under vacuum and then co-evaporated several times with ethanol to give 520 mg of a colourless oil identified as N-(2-hydroxyethyl)sulfamide.

| Elemental analysis: | | | | |
|---|---|---|---|---|
| % | C | H | O | S |
| Calculated | 17.1 | 5.8 | 34.2 | 22.9 |
| Experimental | 17.06 | 5.4 | 35 | 23 |

Example 5

Synthesis of N-(2,3-dihydroxypropyl)sulfamide (Compound 4)

Procedure identical to that for N-(2-hydroxyethyl)sulfamide of Example 4, with 2,3-dihydroxypropylamine as amine, which gives the compound: N-(tert-butoxycarbonyl)-N"-(2,3-dihydroxypropyl)sulfamide, which is then deprotected with hydrochloric acid as for the compound of Example 5, to give a colourless oil identified as N-(2,3-dihydroxypropyl)sulfamide.

| Elemental analysis: Presence of 0.75 H$_2$O per mole | | | | | |
|---|---|---|---|---|---|
| % | C | H | N | O | S |
| Calculated | 21.1 | 5.9 | 16.4 | 37.6 | 18.8 |
| Calculated with 0.75 H$_2$O | 19.6 | 6.2 | 15.2 | 41.4 | 17.4 |
| Experimental | 19.9 | 5.8 | 14.8 | 38.3 | 17.3 |

Example 6

Synthesis of N-[bis(trimethylsilyl)methyl]sulfamide (Compound 9)

The procedure is identical to that for the compound of Example 4, with bis(trimethylsilyl)methylamine as amine, to give the protected compound: N-(tert-butoxycarbonyl)-N"-(bis(trimethylsilyl)methyl)sulfamide.

However, the deprotection process is performed differently. To a solution of 30 ml of dichloromethane and 30 ml trifluoroacetic acid are added, at 0° C., 2 grams of N-(tert-butoxycarbonyl)-N"-(bis(trimethylsilyl)methyl)sulfamide. The reaction progress is monitored by thin-layer chromatography. After reacting overnight, the reaction medium is concentrated under vacuum, taken up and co-evaporated with diethyl ether and dichloromethane. The paste obtained is then purified on a column of silica to give 500 mg of a white solid identified as N-[bis(trimethylsilyl)methyl]sulfamide.

Melting point: 76-77.5° C. (dichloromethane).

| Elemental analysis: | | | | |
|---|---|---|---|---|
| % | C | H | N | S |
| Calculated | 33 | 8.7 | 11 | 12.6 |
| Experimental | 33 | 8.5 | 11.1 | 11.9 |

Example 7

Synthesis of N-[bis(trimethylsilyl)methyl]-N"-(2-hydroxyethyl)sulfamide (Compound 15)

To 2.18 ml of chlorosulfonyl isocyanate in 10 ml of dichloromethane is added dropwise, at 0° C., a solution of 1.77 ml of bromoethanol in 10 ml of dichloromethane. The reaction medium is stirred for 10 minutes at 0° C. and then added dropwise to a solution of 4.38 grams of bis(trimethylsilyl) methylamine and 3.51 ml of triethylamine in 40 ml of dichloromethane at 0° C. After warming to 20° C. and stirring for 4 hours, the reaction mixture is cooled to 0° C. and 10.5 ml of triethylamine are then added dropwise. The reaction mixture is then stirred overnight at room temperature. It is then diluted with dichloromethane and washed 3 times with dilute hydrochloric acid. The organic phase is then washed once with saturated aqueous NaCl solution and then dried over sodium sulfate and concentrated under reduced pressure to give a white solid, 2-oxooxazolidine-3-sulfonic acid [bis(trimethylsilanyl)methyl]amide (65% yield).

To 1 g of 2-oxooxazolidine-3-sulfonic acid [bis(trimethylsilanyl)methyl]amide suspended in 4 ml of ethanol are added 10 ml of 2N sodium hydroxide at room temperature. The reaction mixture is thus stirred for 2 days at room temperature to convert the product. The reaction medium is extracted 3 times with ethyl acetate. The organic phase is dried over sodium sulfate and concentrated under vacuum to give a solid, which is then washed with a pentane/ether mixture.

Melting point: 104-106° C. (pentane/ether).

| Elemental analysis: | | | | |
|---|---|---|---|---|
| % | C | H | N | S |
| Calculated | 36.2 | 8.8 | 9.4 | 10.7 |
| Experimental | 35.7 | 8.66 | 9.3 | 10.79 |

Example 8

Synthesis of N,N'-bis(2-hydroxyethyl)sulfamide (Compound 10)

17 g of sulfonylbisoxazolidinone are added to 2N sodium hydroxide solution (170 ml of water for 13.6 g of NaOH) and placed under stirring. After a strong evolution of $CO_2$, the reaction medium is stirred for 3 days at room temperature. The reaction medium is then passed through Dowex® 50WX8-200 resin (sold by Aldrich). The resin is filtered through a sinter funnel and the filtrate is concentrated under vacuum. The residue is purified by flash chromatography on silica (eluent: 8/2 EtOAc/MeOH). The volatile materials are evaporated off under vacuum to give a colourless oil (87% yield).

| Elemental analysis: | | | | | |
|---|---|---|---|---|---|
| % | C | H | N | O | S |
| Calculated pure product | 26 | 6.5 | 15.2 | 34.7 | 17.4 |
| Calculated product with 0.5 mol of water | 24.9 | 6.7 | 14.5 | 37.3 | 16.6 |
| Experimental | 25 | 6.6 | 14.5 | 36.7 | 17 |

Example 9

Evaluation of the Moisturizing Potential

Two tests were performed to evaluate the moisturizing potential of the compounds of the invention formulated in an aqueous 3% solution (except for compounds 9 and 15, which were evaluated in a solution of isopropyl N-lauroyl sarcosinate).

Dermometer, mechanical measurement of the plasticizing effect (described by J. de Rigal, J-L. Leveque, *International Journal of Cosmetic Science*, 1982, 247-260), Transepidermal Water Loss (TWL), evaluation of the changes in barrier function of the stratum corneum.

Dermometer

The tests carried out were performed under standard conditions on stratum corneum in a room with regulated temperature and humidity (T=30° C. and RH=75%). The modulus of elasticity measurements are performed on each control specimen and then 2 hours and 20 hours after application of the treatment. The relative variation in the modulus allows assessment of the plasticizing effect of the active agent on the stratum corneum.

Transepidermal Water Loss (TWL)

Transepidermal water loss is a physiological phenomenon of diffusion of water vapour across the horny layer. It results from the presence of a high pressure gradient of water vapour between the internal and external media of the body. The TWL depends on the integrity of the barrier function of the stratum corneum. The machine evaluating the TWL (Evaporimeter EP1, Servomed) measures the flow of water that diffuses passively across the stratum corneum ($g/m^2/h$).

The isolated stratum is placed (inner face) on a water tank and equilibrated in a room regulated at 40% relative humidity (T=30° C.). Before the measurement, the stratum corneum is defatted via a two-hour treatment in a mixture of chloroform and methanol (2 v/1 v). For each measurement, the TWL is measured on the stratum corneum before treatment and then 2 and 20 hours after application of the treatment. The relative variation in the TWL allows assessment of the change in the barrier property of the stratum corneum. The measurements are analysed in pairs. For each product, 8 measurements are taken on 2 batches of stratum corneum.

The technique allows measurement of the flow of water that diffuses passively across a membrane of stratum corneum. This measurement takes into account the integrity of the barrier function of the stratum corneum. In the protocol used, the stratum corneum is defatted via a two-hour treatment in a mixture of chloroform and methanol (2 v/1 v). The measurements are taken on the control stratum corneum and then 2 hours and 20 hours after application of the product. The relative variation in the TWL allows assessment of the change in the barrier property of the stratum corneum.

Table 2: Dermometer measurements: Relative variation in the modulus of elasticity of stratum corneum at 30° C. and 75% relative humidity, 2 hours and 20 hours after application of the active agent.

TABLE 2

| Product | Mean ± standard deviation | |
|---|---|---|
| | 2 h | 20 h |
| 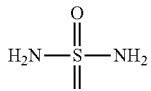 No. 1 | −57 ± 7% | −68 ± 8% |
| 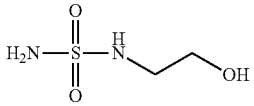 No. 2 | −46 ± 13% | −63 ± 14% |
| 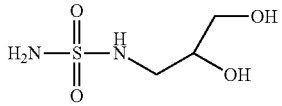 No. 4 | −41 ± 17% | −54 ± 15% |
| 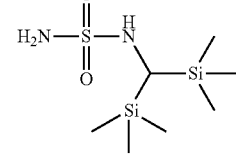 No. 9 | −25 ± 19% | −34 ± 19% |
| 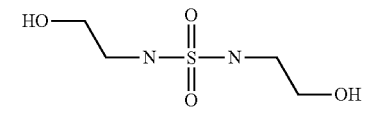 No. 10 | −40 ± 16% | −49 ± 14% |
| 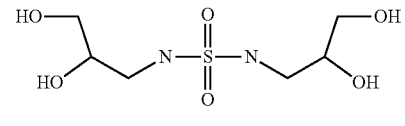 No. 13 | −27 ± 15% | −29 ± 13% |
| 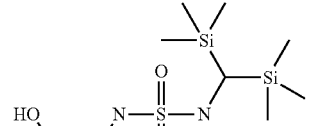 No. 15 | −28 ± 15% | −31 ± 24% |

TABLE 2-continued

| Product | 2 h | 20 h |
|---|---|---|
| 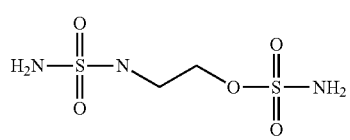 No. 17 | −34 ± 14% | −44 ± 14% |
| 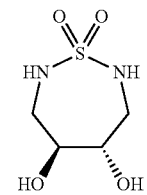 No. 19 | −20 ± 6% | −24 ± 10% |
| Control products | | |
| Untreated stratum corneum | −4 ± 5% | −10 ± 5% |
| Pure water | −5 ± 10% | −2 ± 12% |
| Isopropyl N-lauroylsarcosinate[1] | −18 ± 18% | −20 ± 22% |
| 3% urea in water | −72 ± 9% | −83 ± 7% |
| 3% glycerol in water | −41 ± 12% | −51 ± 15% |

[1] sold under the name Eldew SL205 ® by the company Ajinomoto.

The mean and the standard deviation were calculated on 6 to 10 samples.

Table 3: Relative variation of the TWL measurements 2 hours and 20 hours after application of the active agent

TABLE 3

| Product | (Mean ± standard deviation) | |
|---|---|---|
| | 2h | 20h |
| 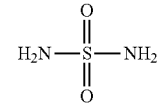 No. 1 | 42.4 ± 22.6% | 37.1 ± 21.1% |
| 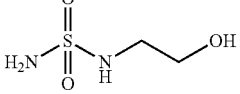 No. 2 | 38 ± 18% | 37 ± 17% |
| 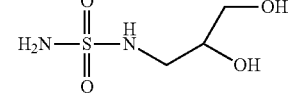 No. 4 | 13 ± 11% | 1 ± 10% |

TABLE 3-continued

| Structure | | |
|---|---|---|
| No. 9 (H₂N-S(=O)₂-N with CH(Si(CH₃)₃)(Si(CH₃)₃) group) | −3 ± 5% | −4.5 ± 5% |
| No. 10 (HO-CH₂CH₂-N(H)-S(=O)₂-N(H)-CH₂CH₂-OH) | 31.5 ± 22.1% | 21.1 ± 6.0% |
| No. 13 (HO-CH₂-CH(OH)-CH₂-N(H)-S(=O)₂-N(H)-CH₂-CH(OH)-CH₂-OH) | 4.6 ± 9.4% | 1.0 ± 6.0% |
| No. 15 (HO-CH₂CH₂-N(H)-S(=O)₂-N(H)-CH(Si(CH₃)₃)(Si(CH₃)₃)) | 1 ± 8% | 1 ± 5% |
| No. 17 (H₂N-S(=O)₂-N(H)-CH₂CH₂-O-S(=O)₂-NH₂) | 18 ± 15% | −0.5 ± 10% |

| Control products | | |
|---|---|---|
| Pure water | 3.5 ± 10% | −1.7 ± 5.1% |
| Isopropyl N-lauroylsarcosinate[1] | 0.2 ± 7% | −7 ± 4% |
| 3% urea in water | 64.3 ± 26.9% | 48.3 ± 24.5% |
| 3% glycerol in water | 41.2 ± 19.0% | 33.1 ± 20.3% |

[1] sold under the name Eldew SL205 ® by the company Ajinomoto.

The mean and the standard deviation were calculated on 8 samples distributed over 2 batches of stratum corneum.

It emerges from these tests that the compounds according to the invention have different "moisturizing" profiles by plasticizing the stratum corneum and by modifying or not modifying the barrier function.

Example 10

Cosmetic Formulations

Example 10.1

Skincare Cream

| PHASE A | |
|---|---|
| Glyceryl stearate (and) PEG-100 stearate | 2.00 g |
| Dimyristyl tartrate (and) cetearyl alcohol (and) C12-15 pareth-7 (and) PPG-25 laureth-25 | 1.50 g |
| Cyclohexasiloxane | 5.00 g |
| Stearyl alcohol | 1.00 g |
| PHASE B | |
| Water | QS 100 g |
| Pentasodium ethylene diamine tetramethylene phosphate | 0.05 g |
| Ammonium polyacryldimethyltauramide: | 0.40 g |
| Xanthan gum | 0.20 g |
| PHASE C | |
| Compound 4 | 3.00 to 5.00 g |
| Glycerol | 1.50 g |
| Adenosine | 0.10 g |
| Water | 3.00 g |

Procedure

Phase B is heated to about 75° C. and the ammonium polyacryldimethyltauramide is incorporated therein; the mixture is stirred until a homogeneous gel is obtained.

Phase A is heated to about 75° C.

The emulsion is prepared by incorporating Phase A into Phase B.

At 40-45° C., Phase C is incorporated, and stirring is continued until the mixture has completely cooled.

Skincare creams were also prepared according to this formulation with compounds 1, 3, 6, 7, 9, 13, 15, 16 and 19.

| Example 10.2: Skincare cream | |
|---|---|
| Compound 2 | 3.0 to 6.0% |
| Glyceryl monostearate | 0.8% |
| Cetyl alcohol | 2.0% |
| Stearyl alcohol | 5.0% |
| Polyoxyethylene stearate (20 OE) | 3.0% |
| Crosslinked acrylic acid (Carbopol 941) | 0.3% |
| Caprylic/capric triglycerides | 12.0% |
| Preserving agents qs | |
| Water qs | 100.0% |

Skincare creams were also prepared according to this formulation with compounds 5, 8, 10, 11, 12, 14, 17 and 18.

The illustrated cosmetic formulations applied to the skin show a good skin moisturizing effect.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A composition, comprising an active ingredient, wherein:
    the active ingredient comprises at least one member selected from the group consisting of compounds of formula (III), salts thereof, and isomers thereof; and
    formula (III) is

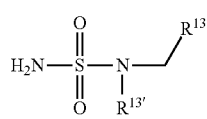

(III)

where:
    $R^{13}$ represents a $(C_1\text{-}C_9)$ alkyl group substituted with 1 to 5 groups selected from the group consisting of —$OR^5$ groups and —O—$SO_2NRR'$ groups;
    $R^{13'}$ represents a hydrogen atom or a $(C_1\text{-}C_4)$ alkyl group;
    $R^5$ represents a hydrogen atom, a $(C_2\text{-}C_4)$ alkyl group, a —$SO_2NRR'$ group, or a $SiR^8R^9R^{10}$ group;
    $R^8$, $R^9$ and $R^{10}$ each independently represents a $(C_1\text{-}C_4)$ alkyl group; and
    R and R' each independently represents a hydrogen atom or a $(C_1\text{-}C_4)$ alkyl group.

2. The composition according to claim 1, wherein:
    $R^{13}$ represents a $(C_1\text{-}C_9)$ alkyl group substituted with at least one of 1 to 5 hydroxyl groups and a —O—$SO_2NH_2$ group; and
    $R^{13'}$ represents a hydrogen atom or a methyl group.

3. The composition according to claim 1, wherein the composition is a cosmetic composition.

4. The composition according to claim 3, further comprising at least one of:
    a skin moisturizer; and
    at least one active agent selected from the group consisting of active agents that affect a barrier function of the skin, active agents that promote skin moisturization, and desquamating agents.

5. The composition according to claim 3, wherein the composition is formulated for non-therapeutic skincare.

6. The composition according to claim 3, further comprising at least one ingredient selected from the group consisting of oils, fatty substances, emulsifiers, gelling agents, film-forming polymers, preserving agents, solvents, fragrances, fillers, UV-screening agents, bactericides, odor absorbers, dyestuffs, plant extracts, and salts.

7. A cosmetic treatment process for non-therapeutic skincare and/or for making up the skin, comprising applying the composition according to claim 1 to the skin.

8. The cosmetic treatment process according to claim 7, comprising applying the cosmetic composition to moisturize the skin.

9. A method for manufacturing a cosmetic composition, comprising combining an active ingredient with a physiologically acceptable medium, wherein:
    the active ingredient comprises at least one member selected from the group consisting of compounds of formula (III) and salts thereof; and
    formula (III) is

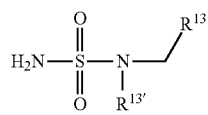

(III)

where:
    $R^{13}$ represents a $(C_1\text{-}C_9)$ alkyl group substituted with 1 to 5 groups selected from the group consisting of —$OR^5$ groups and —O—$SO_2NRR'$ groups;
    $R^{13'}$ represents a hydrogen atom or a $(C_1\text{-}C_4)$ alkyl group;
    $R^5$ represents a hydrogen atom, a $(C_2\text{-}C_4)$ alkyl group, a —$SO_2NRR'$ group, or a $SiR^8R^9R^{10}$ group;
    $R^8$, $R^9$ and $R^{10}$ each independently represents a $(C_1\text{-}C_4)$ alkyl group; and
    R and R' each independently represents a hydrogen atom or a $(C_1\text{-}C_4)$ alkyl group.

10. The method according to claim 9, wherein:
    $R^{13}$ represents a $(C_1\text{-}C_9)$ alkyl group substituted with at least one of 1 to 5 hydroxyl groups or a —O—$SO_2NH_2$ group; and
    $R^{13'}$ represents a hydrogen atom or a methyl group.

11. The method according to claim 9, wherein the cosmetic composition is formulated as a moisturizer.

12. The method according to claim 9, further comprising combining with the physiologically acceptable medium at least one of:
    (a) a skin moisturizer; and
    (b) at least one active agent selected from the group consisting of active agents that affect a barrier function of the skin, active agents that promote skin moisturization, and desquamating agents.

13. The method according to claim 9, wherein the composition is formulated for non-therapeutic skincare.

14. The method according to claim 9, further comprising combining at least one ingredient selected from the group consisting of oils, fatty substances, emulsifiers, gelling agents, film-forming polymers, preserving agents, solvents, fragrances, fillers, UV-screening agents, bactericides, odor absorbers, dyestuffs, plant extracts, and salts with the physiologically acceptable medium.

15. A compound of formula (III) or a salt thereof,

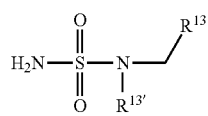

(III)

where;
    $R^{13}$ represents a $(C_1\text{-}C_9)$ alkyl group substituted with 1 to 5 groups selected from the group consisting of —$OR^5$ groups and —O—$SO_2NRR'$ groups;

$R^{13\prime}$ represents a hydrogen atom or a ($C_1$-$C_4$) alkyl group;
$R^5$ represents a hydrogen atom, a ($C_2$-$C_4$) alkyl group, a -$SO_2NRR'$ group, or a $SiR^8R^9R^{10}$ group;
$R^8$, $R^9$ and $R^{10}$ each independently represents a ($C_1$-$C_4$) alkyl group; and
R and R' each independently represents a hydrogen atom or a ($C_1$-$C_4$) alkyl group.

16. The compound or salt according to claim 15, wherein:
$R^{13}$ represents a ($C_1$-$C_9$) alkyl group substituted with at least one of 1 to 5 hydroxyl groups and a —O—$SO_2NH_2$ group; and
$R^{13\prime}$ represents a hydrogen atom or a methyl group.

* * * * *